United States Patent [19]

Hatae

[11] Patent Number: 4,919,921

[45] Date of Patent: Apr. 24, 1990

[54] COMPOSITIONS FOR TOPICAL USE HAVING MELANIN SYNTHESIS-INHIBITING ACTIVITY

[75] Inventor: Shinkichi Hatae, Onojo, Japan

[73] Assignee: Sansho Seiyaku Co., Ltd., Onojo, Japan

[21] Appl. No.: 248,684

[22] Filed: Sep. 23, 1988

[30] Foreign Application Priority Data

Sep. 25, 1987 [JP] Japan .................................. 62-241965

[51] Int. Cl.$^5$ ................................................ A61K 7/48
[52] U.S. Cl. ..................................... 424/62; 514/474; 514/460
[58] Field of Search .................... 424/62, 59; 514/460, 514/474

[56] References Cited

U.S. PATENT DOCUMENTS

| | | | |
|---|---|---|---|
| 4,278,656 | 7/1981 | Nagai et al. | 424/62 |
| 4,369,174 | 1/1983 | Nagai et al. | 424/62 |
| 4,818,521 | 4/1989 | Tamabuchi | 424/62 |

FOREIGN PATENT DOCUMENTS

| | | | |
|---|---|---|---|
| 2744976 | 4/1979 | Fed. Rep. of Germany | 514/474 |
| 53-18739 | 2/1978 | Japan . | |
| 56-7776 | 1/1981 | Japan . | |
| 56-79616 | 6/1981 | Japan . | |
| 59-33207 | 2/1984 | Japan . | |
| 59-157009 | 9/1984 | Japan . | |
| 100509 | 5/1986 | Japan | 514/474 |
| 2052973 | 2/1981 | United Kingdom . | |

OTHER PUBLICATIONS

Patents Abstracts of Japan, vol. 10, No. 103.
Chemical Abstracts, vol. 75 (108393t).
Chemical Abstracts, vol. 69 (41399e).

*Primary Examiner*—Henry F. Epstein
*Assistant Examiner*—Susan S. Rucker
*Attorney, Agent, or Firm*—Armstrong, Nikaido, Marmelstein, Kubovcik & Murray

[57] ABSTRACT

Compositions for topical use having melanin synthesis-inhibiting activity comprising kojic acid or its esters and vitamin C or its derivatives. The compositions have excellent human skin-whitening effect and anti-suntan effect.

5 Claims, No Drawings

COMPOSITIONS FOR TOPICAL USE HAVING MELANIN SYNTHESIS-INHIBITING ACTIVITY

BACKGROUND OF THE INVENTION

The present invention relates to compositions for external use having a melanin synthesis-inhibiting activity, which can be formulated in cosmetic compositions or ointments to exhibit a human skin-whitening effect and anti-suntan effect.

It is known that kojic acid and its ester have an effect to inhibit synthesis of melanin (Japanese Tokkyo Kokai No. 18739/1978, No. 7776/1981, No. 79616/1981, No. 33207/1984).

Kojic acid or its esters have an action to inhibit an activity of tyrosinase which is the enzyme to convert tyrosine to dopa, then to dopa quinone in the pathway of melanin synthesis, whereby the synthesis of melanin is prevented.

The present inventor has intensively studied the kojic acid or its esters, in order to obtain more effective melanin synthesis-inhibiting activity, by producing various derivatives of kojic acid or its esters or by using with other drugs. As a result of the study, it has been found a surprising fact that the melanin synthesis can be synergistically inhibited by blending vitamin C or its derivatives with kojic acid or its esters, and then the present invention has been completed.

SUMMARY OF THE INVENTION

According to the present invention there can be provided compositions for topical use having the melanin synthesis-inhibiting activity comprising an effective amount of kojic acid or its esters and vitamin C or its derivatives.

DETAILED DESCRIPTION

As mentioned above it has been known that the kojic acid and its esters have the melanin synthesis-inhibiting activity, and also that a large dose of vitamin C can exhibit a whitening effect of human skin. When the two compounds are blended, however, the blended agent can give a surprising effect which is not an additive effect by a synergistic effect, i.e. as explained hereinafter the excellent effect can be obtained by blending a small amount of vitamin C. Though the mechanism of this synergistic effect has not yet been clear, it is seemed that a certain delicate correlation occurs in addition to a complementary effect in which a part of effect which cannot be covered with one compound is covered with the other compound.

The kojic acid or its esters which is one of the active ingredients of the present invention is preferably represented by the formula:

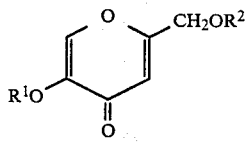

wherein $R^1$ and $R^2$ are the same or different, and each is hydrogen atom or an acyl group of 3 to 20 carbon atoms.

Non-exclusive examples of the esters are, for instance, kojic acid monoesters such as kojic acid monobutyrate, kojic acid monocaprate, kojic acid monopalmitate, kojic acid monostearate, kojic acid monocinnamoate and kojic acid monobenzoate; kojic acid diesters such as kojic acid dibutyrate, kojic acid dipalmitate, kojic acid distearate and kojic acid dioleate. Preferred monoester is an ester in which a OH group at 5-position of kojic acid is esterified. Esterification can improve stabilities against pH or sun light, while maintaining a melanin synthesis-inhibiting activity equal to that of kojic acid.

Another active ingredient is vitamin C or its derivatives. Non-exclusive examples of the derivatives are, for instance, alkyl esters of L-ascorbic acid such as L-ascorbyl palmitate, L-ascorbyl isopalmitate, L-ascorbyl dipalmitate, L-ascorbyl diisopalmitate, L-ascorbyl stearate, L-ascorbyl isostearate, L-ascorbyl distearate, L-ascorbyl diisostearate, L-ascorbyl myristate, L-ascorbyl isomyristate, L-ascorbyl dimyristate, L-ascorbyl diisomyristate, L-ascorbyl 2-ethylhexanoate, L-ascorbyl di-2-ethylhexanoate, L-ascorbyl oleate and L-ascorbyl dioleate; phosphates of L-ascorbic acid such as L-ascorbyl-2-phosphate and L-ascorbyl-3-phosphate; sulfates of L-ascorbic acid such as L-ascorbyl-2-sulfate and L-ascorbyl-3-sulfate; their salts with alkali metals such as sodium and pottasium; and their salts with alkaline earth metals such as calcium and magnesium. They can be used alone or in a mixture of two or more.

The comoposition for topical use of the present invention comprises the kojic acid or its ester and the vitamin C or its derivative, and may be prepared in various forms which can exhibit the melanin synthesis-inhibiting activity and whitening effect and anti-suntan effect, e.g. in a form of cosmetic preparation such as cream, cosmetic lotion, pack or powder, or in a form of quasidrug such as emulsion, lotion, liniment or ointment. In each formulation, there may be used usual additives such as base material, excipient, stabilizer, pigment, fragrance, UV-absorbent, antioxidant, antiseptics, metal deactivator and organic acid.

Mixing ratio of kojic acid or its esters to vitamin C or its derivatives varies with their kind or combination, and is generally 1:0.01 to 1:20 by weight, preferably 1:0.1 to 1:10. Total amount of the active ingredients varies with manner of use, object of use, method of use and preparation form, and is, for example, in cosmetics 0.01 to 20% (% by weight, hereafter the same), preferably 0.5 to 10%, and in ointments 0.01 to 10%, preferably 0.5 to 5%.

The active ingredients of the present invention, i.e. kojic acid, its esters, vitamin C and its derivatives are non toxic to human, and also mixture thereof can be used without any trouble.

The present invention is more specifically described and explained by means of the following Examples. It is to be understood that the present invention is not limited to those Examples, and may be made various changes and modifications without departing from the scope or spirit of the present invention.

EXAMPLE 1

B-16 Cultured cells derived from mouse melanoma cells were inoculated in Eagle's minimum essential medium containing 10% fetal bovine serum to which kojic acid and vitamin C or its derivative are added in an amount shown in Table 1. The B-16 cells were cultured for 5 days at 37° C. under 5% $CO_2$ atmosphere, then dispersed with trypsin, and then centrifuged at 1,000 rpm for 5 minutes to collect the cells. Darkness of the cell pellet was observed with naked eyes, and evaluated according to the following standard.

- —: Same color as that when a melanin synthesis-inhibiting agent is not added.
- +: Slightly whitened.
- + +: Considerably whitened.
- + + +: Almost whitened.

The results are shown in Table 1.

TABLE 1

| Vitamin C or its derivative | | Concentration of | |
|---|---|---|---|
| Kind | Concentration (mM) | Kojic acid (mM) | Depigmenting Effect |
| — | — | 0.5 | ± |
| — | — | 1.0 | + |
| Vitamin C | 0.2 | — | — |
|  | 0.4 | — | — |
|  | 0.2 | 0.5 | + |
|  | 0.4 | 0.5 | + + |
| Magnesium salt of L-ascorbyl-2-phosphate | 0.5 | — | — |
|  | 1.0 | — | — |
|  | 0.5 | 0.5 | + |
|  | 1.0 | 0.5 | + + |
| Sodium salt of L-ascorbyl-2-sulfate | 0.5 | — | — |
|  | 1.0 | — | — |
|  | 0.5 | 0.5 | + |
|  | 1.0 | 0.5 | + + |

EXAMPLE 2

On the inner side of right upper arm of each volunteer (thirty healthy men and women), a test site (2 cm × 2 cm) was provided. Before irradiation with ultraviolet rays the test site was carefully washed with warm water and was wrapped around the test site with aluminum foil so that only the test site was irradiated with ultraviolet rays. The irradiation was carried out three consecutive days at a dose of $0.8 \times 10^7$ erg/cm$^3$ per each irradiation per one day with four lamps (FL20S.BLB Lamp×2 and FL20S.E-30 Lamp×2 available from Toshiba Co., Ltd.) which were set at a distance of 10 cm from the test site. After the irradiation, the following test composition (vanishing cream) was applied everyday to the irradiated site three times per day (morning, noon, night). After three weeks, degree of pigmentation of the test site was observed with naked eyes. The improvement of the pigmentation was evaluated by the number of volunteers in three degrees, i.e. very effective, effective or non-effective. The results are shown in Table 2.

| (Test composition) | Part by weight |
|---|---|
| (A) Kojic acid ester shown in Table 2 | 1.00 |
| Polyoxyethylene (40) monostearate | 2.00 |
| Glycerol monostearate (selfemulsifying type) | 5.00 |
| Stearic acid | 5.00 |
| Behenyl alcohol | 1.00 |
| Liquid paraffin | 1.00 |
| Glyceryl trioctanoate | 10.00 |
| Antiseptics | proper |
| Fragrance | slight |
| (B) Vitamn C or its derivative shown in Table 2 | 1.00 |
| 1,3-Butylene glycol | 5.00 |
| Purified water | remain |

PREPARATION

The ingredients (A) are melted by heating to obtain an oil phase. Separately the ingredients (B) are dissolved by heating to prepare an aqueous phase. The aqueous phase is added to the oil phase, and the resulting mixture is emulsified with stirring, then cooled to give a vanishing cream.

TABLE 2

| Kojic acid ester | Vitamin C and its derivative | Number of the volunteers | | |
|---|---|---|---|---|
| | | Very effective | Effective | Non-effective |
| — | Vitamin C | 0 | 8 | 22 |
| — | L-Ascorbyl dipalmitate | 0 | 7 | 23 |
| — | L-Ascorbyl stearate | 0 | 8 | 22 |
| — | L-Ascorbyl-2-phosphate | 0 | 10 | 20 |
| — | L-Ascorbyl-2-sulfate | 0 | 8 | 22 |
| Kojic acid monostearate | — | 3 | 6 | 21 |
| " | Vitamin C | 5 | 11 | 14 |
| " | L-Ascorbyl dipalmitate | 4 | 10 | 16 |
| " | L-Ascorbyl stearate | 5 | 11 | 14 |
| " | L-Ascorbyl-2-phosphate | 6 | 12 | 12 |
| " | L-Ascorbyl-2-sulfate | 5 | 10 | 15 |
| Kojic acid dipalmitate | — | 2 | 8 | 20 |
| " | Vitamin C | 4 | 12 | 14 |
| " | L-Ascorbyl dipalmitate | 5 | 11 | 14 |
| " | L-Ascorbyl stearate | 4 | 10 | 16 |
| " | L-Ascorbyl-2-phosphate | 5 | 13 | 12 |
| " | L-Ascorbyl-2-sulfate | 5 | 13 | 12 |

The followings are typical formulations of the melanin synthesis-inhibiting agent of the present invention. It is to be understood that the present invention is not limited to the formulations.

| Lotion | Part by weight |
|---|---|
| Polyoxyethylene (60) hydrogenated castor oil | 1.00 |
| Ethanol | 15.00 |
| Citric acid | 0.10 |
| Sodium citrate | 0.30 |
| 1,3-Butylene glycol | 4.00 |
| Kojic acid | 1.00 |
| Sodium salt of L-ascorbyl-2-phosphate | 2.00 |
| Antiseptics | proper |
| Fragrance | slight |
| Purified water | remain |

PREPARATION

The all ingredients are homogeneously mixed and dissolved with stirring to give a lotion.

| Emulsion | Part by weight |
| --- | --- |
| (A) Polyoxyethylene (20) behenyl ether | 0.50 |
| Polyoxyethylene (60) sorbitol tetraoleate | 1.00 |
| Glyceryl monostearate (hydrophilic type) | 1.00 |
| Stearic acid | 0.50 |
| Behenyl alcohol | 0.50 |
| Avocado oil | 1.00 |
| Natural vitamin E | 0.02 |
| Kojic acid monopalmitate | 2.00 |
| Antiseptics | proper |
| Fragrance | slight |
| (B) 1,3-Butylene glycol | 5.00 |
| Carboxyvinyl polymer | 0.10 |
| Sodium N-lauroyl-L-glutamate | 0.50 |
| Magnesium salt of L-ascorbyl-2-phosphate | 1.00 |
| Purified water | remain |

PREPARATION

The ingredients (A) are melted by heating to obtain an oil phase. Separately the ingredients (B) are dissolved by heating to prepare an aqueous phase. The aqueous phase is added to the oil phase, and the resulting mixture is emulsified with stirring, then cooled to give an emulsion.

| Jellied pack | Part of weight |
| --- | --- |
| Citric acid | 0.20 |
| Propylene glycol | 4.00 |
| Glycerin | 4.00 |
| Ethanol | 2.00 |
| Carboxyvinyl polymer | 1.00 |
| Pottasium carbonate | 0.60 |
| Kojic acid | 0.50 |
| Magnesium salt of L-ascorbyl-2-sulfate | 0.50 |
| Antiseptics | proper |
| Fragrance | slight |
| Purified water | remain |

PREPARATION

The all components are homogeneously mixed and dissolved with stirring to give a jellied pack.

| Creamy pack | Part by weight |
| --- | --- |
| (A) Poyoxyethylene (20) behenyl ether | 1.00 |
| Polyoxyethylene (40) sorbitol tetraoleate | 2.00 |
| Glycerin monostearate (hydrophilic type) | 2.00 |
| Behenyl alcohol | 3.00 |
| Squalane | 25.00 |
| Glycerine octanoate | 10.00 |
| Natural vitamin E | 0.04 |
| Kojic acid monocinnamoate | 2.00 |
| L-Ascorbyl dipalmitate | 0.50 |
| Antiseptics | proper |
| Fragrance | slight |
| (B) 1,3-Butylene glycol | 5.00 |
| Sodium dl-pyrrolidonecarboxylate | 1.50 |
| Citric acid | 0.04 |
| L-Ascorbyl-2-phosphate | 0.50 |
| Purifed water | remain |

PREPARATION

The ingredients (A) are melted by heating to obtain an oil phase. Separately, the ingredients (B) are dissolved by heating to prepare an aqueous phase. The aqueous phase is added to the oil phase, and the resulting mixture is emulsified with stirring, then cooled to give a creamy pack.

| Ointment | Part by weight |
| --- | --- |
| (A) Polyoxyethylene (60) sorbitan monostearate | 1.00 |
| Polyoxyethylene (60) sorbitol tetraoleate | 1.50 |
| Glycerin monostearate (selfemulsifying type) | 1.50 |
| Beeswax | 2.00 |
| Paraffin | 2.00 |
| Stearic acid | 3.00 |
| Behenyl alcohol | 3.00 |
| Shea butter | 12.00 |
| Liquid paraffin | 5.00 |
| Natural vitamin E | 0.04 |
| Methyl polysiloxane | 0.01 |
| Kojic acid monobenzoate | 3.00 |
| Antiseptics | proper |
| Fragrance | slight |
| (B) 1,3-Butylene glycol | 5.00 |
| Citric acid | 0.30 |
| Sodium dl-lauroyl-L-glutamate | 0.50 |
| Pottasium salt of L-ascorbyl-2-phosphate | 1.00 |
| Purified water | remain |

PREPARATION

The ingredients (A) are melted by heating to obtain an oil phase. Separately, the ingredients (B) are dissolved by heating to prepare an aqueous phase. The aqueous phase is added to the oil phase, and the resulting mixture is emulsified with stirring, then cooled to give an ointment.

| Whitening powder | Part by weight |
| --- | --- |
| Octyldodecyl myristate | 1.0 |
| Kojic acid | 2.0 |
| L-Ascorbyl stearate | 5.0 |
| Fragrance | slight |
| Maltitol | remain |

PREPARATION

The all ingredients are homogeneously mixed to give a whitening powder.

What is claimed is:

1. A composition for topical use which has a melanin synthesis-inhibiting activity, comprising kojic acid or an ester of kojic acid and vitamin C or or a derivative of vitamin C.

2. The composition of claim 1, wherein the kojic acid or ester of kojic acid is a compound of the formula

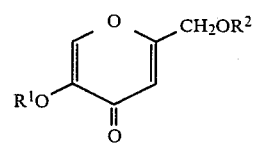

wherein $R^1$ and $R^2$ are the same or different, and each is hydrogen or an acyl group of 3 to 20 carbon atoms.

3. The composition of claim 2, wherein the kojic acid ester is a member selected from the group consisting of kojic acid monobutyrate, kojic acid monocaprate, kojic acid monopalmitate, kojic acid monostearate, kojic acid monocinnamoate, kojic acid monobenzoate, kojic acid dibutyrate, kojic acid dipalmitate, kojic acid distearate, kojic acid dioleate and a mixture thereof.

4. The composition of claim 1, wherein the derivative of vitamin C is a member selected from the group consisting of an alkyl ester of L-ascorbic acid, a phosphate of L-ascorbic acid, a sulfate of L-ascorbic acid, a metal salt thereof and a mixture thereof.

5. A composition for topical use which has a melanin synthesis-inhibiting activity, comprising 1 part by weight of kojic or an ester of kojic acid and 0.01 to 20 parts by weight of vitamin C or a derivative of vitamin C.

* * * * *